(12) United States Patent
Alnemri

(10) Patent No.: US 6,600,024 B1
(45) Date of Patent: Jul. 29, 2003

(54) BLK GENES, GENE PRODUCTS AND USES THEREOF IN APOPTOSIS

(75) Inventor: Emad S. Alnemri, Upper Dublin Township, Montgomery County, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/709,790

(22) Filed: Nov. 7, 2000

Related U.S. Application Data

(62) Division of application No. 09/052,877, filed on Mar. 31, 1998, now Pat. No. 6,190,912.

(51) Int. Cl.[7] .......................... C07K 16/00; C07K 17/00
(52) U.S. Cl. .................. 530/389.7; 530/350; 530/300; 530/327; 435/69.1; 435/325
(58) Field of Search .............................. 435/350, 320.1, 435/325, 69.1; 536/23.1; 530/350, 389.7, 300, 327; 514/2

(56) References Cited

U.S. PATENT DOCUMENTS

| | | | | |
|---|---|---|---|---|
| 5,834,234 A | * | 11/1998 | Gallo | ........................ 435/69.1 |
| 5,955,593 A | * | 9/1999 | Korsmeyer | ................ 536/23.5 |

FOREIGN PATENT DOCUMENTS

| | | | |
|---|---|---|---|
| WO | WO 92/16623 | * | 10/1992 |
| WO | WO 96/35951 | | 11/1996 |
| WO | WO 99/16787 | | 4/1999 |

OTHER PUBLICATIONS

Bork et al. Predicting functions from protein sequences–where are the bottlenecks? pp. 313–318 vol. 18 Apr. 1998.*

Ngo et al. Computational complexity protein structure prediction, and the levinthal paradox pp. 491–495 1994.*

Chiu et al. Optimizing energy potentials for success in protein tertiary structure prediction pp. 223–228 vol. 3 No. 3.*

Anderson, *Nature* 392: 25–30, 1998.

Boyd et al., "Bik, a novel death–inducing protein shares a distinct sequence motif with Bcl–2 family proteins and interacts with viral and cellular survival–promoting proteins," *Oncogene 11*: 1921–1928, 1995.

Chittenden et al., "A conserved domain in Bak, distinct from BH1 and BH2, mediates cell death and protein binding functions," *The EMBO Journal 14*(22): 5589–5596, 1995.

Dymecki et al., "Specific Expression Of A Tyrosine Kinase Gene, blk, In B Lymphoid Cells," *Science 247*(9): 332–336, 1990.

Hawkins and Vaux, "The role of the Bcl–2 family of apoptosis regulatory proteins in the immune system," *Seminars in Immunology 9*: 25–33, 1997.

Hedge et al., "Blk, A BH3–containing Mouse Protein That Interacts With Bcl–2 and BCL–xL, Is A Potent Death Agonist," *The Journal Of Biological Chemistry 273*(14): 7783–7786, 1998.

Hunter and Parslow, "A Peptide Sequence from Bax That Converts Bcl–2 Into an Activator of Apoptosis," *The Journal Of Biological Chemistry 271*(15): 8521–8524, 1996.

Inohara et al., "*harakiri*, a novel regulator of cell death, encodes a protein that activates apoptosis and interacts selectively with survival–promoting proteins Bcl–2 and Bcl–$X_L$," *The EMBO Journal 16*(7): 1686–1694, 1997.

Mastrangelo et al., *Seminars in Oncology 23*(1): 4–21, 1996.

Reed, Double identity for proteins of the Bcl–2 family, *Nature 387*: 773–776, 1997.

Sidorenko et al., "Human Spleen Tyrosine Kinase p72Syk Associates With The Src–Family Kinase p53/56 Lyn And A 1120kDa Phosphoprotein," *Proc. Nat. Acad. Sci. USA 92*: 359–363, 1995.

Srinivasula et al., "Molecular ordering of the Fas–apoptotic pathway: The Fas/APO–1 protease Mch5 is a CrmA–inhibitable protease that activates multiple Ced–3/ICE–like cysteine proteases," *Proc. Nat. Acad. Sci. USA 93*: 14486–14491, 1996.

Wang et al., "BID: a novel BH3 domain–only death agonist," *Genes & Development 10*: 2859–2869, 1996.

Zha et al., "BH3 Domain of BAD Is Required for Heterodimerization with BCL–$X_L$ and Pro–apoptotic Activity," *The Journal Of Biological Chemistry 272*(39): 24101–24104, 1997.

Zha et al., "Proapoptotic Protein Bax Heterodimerizes with Bcl–2 and Homodimerizes with Bax via a Novel Domain (BH3) Distinct from BH1 and BH2," *The Journal Of Biological Chemistry 271*(13): 7440–7444, 1996.

* cited by examiner

*Primary Examiner*—Dave T. Nguyen
(74) *Attorney, Agent, or Firm*—Seed Intellectual Property Law Group PLLC

(57) ABSTRACT

Genes and gene products of Blk, a pro-apoptotic protein in the Bcl-2 gene family, are provided. Effector molecules that either increase or decrease Blk and thus promote or inhibit apoptosis are described. The Blk genes and proteins and effector molecules may be used to treat diseases that have unwanted cell proliferation used to promote cell growth.

4 Claims, 11 Drawing Sheets

GAATTCCGGC CGGCGTCCCA GCCGAGAGGG TGTTCGGGCA GTTCGCCCGC CGCTACGCCA    60

GCTCAGCTTG GCAGAACAC ATG TCG GAG GCG AGA CTT ATG GCC AGA GAC GTC    112
                   Met Ser Glu Ala Arg Leu Met Ala Arg Asp Val
                    1           5                  10

ATC AAG ACT GTT CCA CAC GAC CAG GTC CCC CAA CCT CCA GTG GCC TCT    160
Ile Lys Thr Val Pro His Asp Gln Val Pro Gln Pro Pro Val Ala Ser
            15                  20                  25

GAG ACT CCC AGC ATG AAG GAG CCT GTG AGA GAC GTG GAC CTC ATG GAG    208
Glu Thr Pro Ser Met Lys Glu Pro Val Arg Asp Val Asp Leu Met Glu
        30                  35                  40

TGC GTG GAA GGC AGA AAC CAG GTG GCC TTG AGG CTG GCC TGC ATC GGC    256
Cys Val Glu Gly Arg Asn Gln Val Ala Leu Arg Leu Ala Cys Ile Gly
        45                  50                  55

GAT GAG ATG GAC CTG TGT CTG CGG AGC CCC CGT CTG GTC CAG CTG CCT    304
Asp Glu Met Asp Leu Cys Leu Arg Ser Pro Arg Leu Val Gln Leu Pro
60                  65                  70                  75

GGG ATT GCT ATA CAC AGA CTC GCT GTC ACC TAC AGC CGG ACA GGT GTC    352
Gly Ile Ala Ile His Arg Leu Ala Val Thr Tyr Ser Arg Thr Gly Val
                80                  85                  90

AGA GGT ATT TTC AGG AGC TTG ATT CGA AGC CTC ACC AAC CTC AGG GAA    400
Arg Gly Ile Phe Arg Ser Leu Ile Arg Ser Leu Thr Asn Leu Arg Glu
            95                  100                 105

AAC ATC TGG TCC TGG AGA GTC TTG ACT CCT GGC GCC TGG GTG TCA CCT    448
Asn Ile Trp Ser Trp Arg Val Leu Thr Pro Gly Ala Trp Val Ser Pro
        110                 115                 120

GAC CAG GAC CCT GGG CAG CTG TTT CCG ATG GTG CTG CTG GTC TTC TTG    496
Asp Gln Asp Pro Gly Gln Leu Phe Pro Met Val Leu Leu Val Phe Leu
        125                 130                 135

CTG CTG GGT GGG GCC TGG TAT TTG CAG CTT CAG TGAAGTGCAG CTGGGGCAGG    549
Leu Leu Gly Gly Ala Trp Tyr Leu Gln Leu Gln
140                 145                 150

*Fig. 1A*

```
GCTGGTCCCT GCCCCCCAAC CCCTAGAGGT GCCGGCACCC TAACTGAGGT GTTTTCTGAC   609

TGTCCCCCCC CCTTTTTATA TATATATTTA ACTCAGGATA GTGCTGAGAT TTCATACAGG   669

TTTTCTGGGT TTTTGTAAGG CAAATGAATT CACTGTACCT CAGGAGCATT ACTGGCTAAG   729

TGCCCCTGAG GCTTGGCTGG CCCTTCTTCT CTTGACCCCT GCTCCCTTCC TCTCTGCAGG   789

CTGGTCCTGT GGCCATCAGT GGGGGGAGTG CTGGCCACAC CCCTGTCTGT GAAGCCTTGA   849

GGCACAGGAT CTACTGGACT AGAGTCCTTT GGGGTGGAGA GTTCAATTAA GTGGTGTTTG   909

CAGGCAAGTT CAATAAAATG TTTCCAGCCA GTC                                942
```

Fig. 1B

```
blk  1    MSEARLMARDVI.KTVPHDQVPQPP...VASETPSMK..EPVRDVDLMEC   44
bik  1    MSEVRPLSRDILMETLLYEQLLEPPTMEVLGMTDSEEDLDPMEDFDSLEC   50 blk  45   VEGRNQVALRLACIGDEMDLCLRSPRLVQLPGIAIHRLAVTY...SRTGV   91
bik  51   MEGSDALALRLACIGDEMDVSLRAPRLAQLSEVAMHSLGLAFIYDQTEDI  100
                    *  ** blk  92   RGIFRSLIRSLTNLRENI.WSWRVLTPGAWVSPDQDPGQLFPMVLLVFLL  140
bik  101  RDVLRSFMDGFTTLKENIMRFWRSPNPGSWVSCEQVLLALLLLALLLPL  150 blk  141  LGGAWYLQLQ  150
bik  151  LSGGLHLLLK  160
```

Fig. 2A

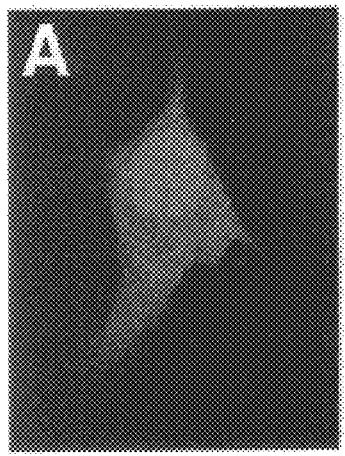
*Fig. 3A*  *Fig. 3B*  *Fig. 3C*
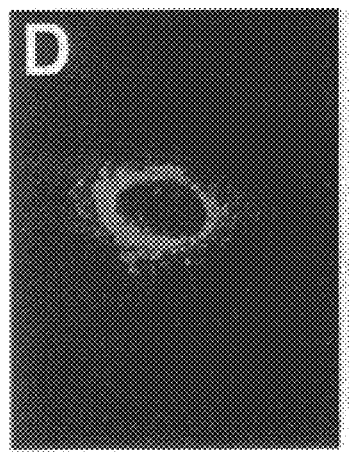
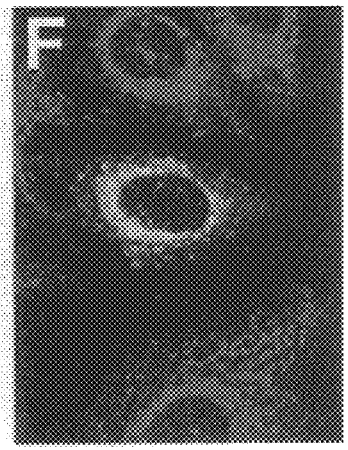
*Fig. 3D*  *Fig. 3E*  *Fig. 3F*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 942 base pairs
      (B) TYPE: nucleic acid
      (C) STRANDEDNESS: single
      (D) TOPOLOGY: linear (ix) FEATURE:
    (A) NAME/KEY: CDS
    (B) LOCATION: 80..529

(xi) SEQUENCE DESCRIPTION: SEQ ID NO: 1:

```
GAATTCCGGC CGGCGTCCCA GCCGAGAGGG TGTTCGGGCA GTTCGCCCGC CGCTACGCCA         60

GCTCAGCTTG GCAGAACAC ATG TCG GAG GCG AGA CTT ATG GCC AGA GAC GTC        112
                    Met Ser Glu Ala Arg Leu Met Ala Arg Asp Val
                     1               5                  10

ATC AAG ACT GTT CCA CAC GAC CAG GTC CCC CAA CCT CCA GTG GCC TCT         160
Ile Lys Thr Val Pro His Asp Gln Val Pro Gln Pro Pro Val Ala Ser
            15                  20                  25

GAG ACT CCC AGC ATG AAG GAG CCT GTG AGA GAC GTG GAC CTC ATG GAG         208
Glu Thr Pro Ser Met Lys Glu Pro Val Arg Asp Val Asp Leu Met Glu
         30                  35                  40

TGC GTG GAA GGC AGA AAC CAG GTG GCC TTG AGG CTG GCC TGC ATC GGC         256
Cys Val Glu Gly Arg Asn Gln Val Ala Leu Arg Leu Ala Cys Ile Gly
     45                  50                  55

GAT GAG ATG GAC CTG TGT CTG CGG AGC CCC CGT CTG GTC CAG CTG CCT         304
Asp Glu Met Asp Leu Cys Leu Arg Ser Pro Arg Leu Val Gln Leu Pro
 60                  65                  70                  75

GGG ATT GCT ATA CAC AGA CTC GCT GTC ACC TAC AGC CGG ACA GGT GTC         352
Gly Ile Ala Ile His Arg Leu Ala Val Thr Tyr Ser Arg Thr Gly Val
                 80                  85                  90

AGA GGT ATT TTC AGG AGC TTG ATT CGA AGC CTC ACC AAC CTC AGG GAA         400
Arg Gly Ile Phe Arg Ser Leu Ile Arg Ser Leu Thr Asn Leu Arg Glu
             95                 100                 105

AAC ATC TGG TCC TGG AGA GTC TTG ACT CCT GGC GCC TGG GTG TCA CCT         448
Asn Ile Trp Ser Trp Arg Val Leu Thr Pro Gly Ala Trp Val Ser Pro
        110                 115                 120

GAC CAG GAC CCT GGG CAG CTG TTT CCG ATG GTG CTG CTG GTC TTC TTG         496
Asp Gln Asp Pro Gly Gln Leu Phe Pro Met Val Leu Leu Val Phe Leu
    125                 130                 135

CTG CTG GGT GGG GCC TGG TAT TTG CAG CTT CAG TGAAGTGCAG CTGGGGCAGG       549
Leu Leu Gly Gly Ala Trp Tyr Leu Gln Leu Gln
140                 145                 150

GCTGGTCCCT GCCCCCCAAC CCCTAGAGGT GCCGGCACCC TAACTGAGGT GTTTTCTGAC       609

TGTCCCCCCC CCTTTTTATA TATATATTTA ACTCAGGATA GTGCTGAGAT TCATACAGG        669

TTTTCTGGGT TTTTGTAAGG CAAATGAATT CACTGTACCT CAGGAGCATT ACTGGCTAAG      729

TGCCCCTGAG GCTTGGCTGG CCCTTCTTCT CTTGACCCCT GCTCCCTTCC TCTCTGCAGG      789

CTGGTCCTGT GGCCATCAGT GGGGGGAGTG CTGGCCACAC CCCTGTCTGT GAAGCCTTGA      849

GGCACAGGAT CTACTGGACT AGAGTCCTTT GGGGTGGAGA GTTCAATTAA GTGGTGTTTG      909

CAGGCAAGTT CAATAAAATG TTTCCAGCCA GTC                                    942
```

(2) INFORMATION FOR SEQ ID NO: 2:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Glu Ala Arg Leu Met Ala Arg Asp Val Ile Lys Thr Val Pro
 1               5                  10                  15
```

```
His Asp Gln Val Pro Gln Pro Val Ala Ser Glu Thr Pro Ser Met
            20                  25                  30

Lys Glu Pro Val Arg Asp Val Asp Leu Met Glu Cys Val Glu Gly Arg
        35                  40                  45

Asn Gln Val Ala Leu Arg Leu Ala Cys Ile Gly Asp Glu Met Asp Leu
    50                  55                  60

Cys Leu Arg Ser Pro Arg Leu Val Gln Leu Pro Gly Ile Ala Ile His
65                  70                  75                  80

Arg Leu Ala Val Thr Tyr Ser Arg Thr Gly Val Arg Gly Ile Phe Arg
                85                  90                  95

Ser Leu Ile Arg Ser Leu Thr Asn Leu Arg Glu Asn Ile Trp Ser Trp
            100                 105                 110

Arg Val Leu Thr Pro Gly Ala Trp Val Ser Pro Asp Gln Asp Pro Gly
        115                 120                 125

Gln Leu Phe Pro Met Val Leu Leu Val Phe Leu Leu Leu Gly Gly Ala
    130                 135                 140

Trp Tyr Leu Gln Leu Gln
145                 150

(2) INFORMATION FOR SEQ ID NO: 3:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 3:

Ala Leu Arg Leu Ala Cys Ile Gly Asp Glu Met Asp
1               5                   10

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO: 4:

NNNBNGUCNN NNNNNN                                                    16

(2) INFORMATION FOR SEQ ID NO: 5:

(i) SEQUENCE CHARACTERISTICS:
        (A) LENGTH: 160 amino acids
        (B) TYPE: amino acid
        (C) STRANDEDNESS: <Unknown>
        (D) TOPOLOGY: linear (xi) SEQUENCE DESCRIPTION: SEQ ID NO: 5:

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60
```

-continued

```
Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
                100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
        130                 135                 140

Ala Leu Leu Leu Pro Leu Leu Ser Gly Gly Leu His Leu Leu Leu Lys
145                 150                 155                 160
```

BLK GENES, GENE PRODUCTS AND USES THEREOF IN APOPTOSIS

CROSS-REFERENCE TO RELATED APPLICATION

This application is a divisional of U.S. patent application Ser. No. 09/052,877, filed Mar. 31, 1998, and issued as U.S. Pat. No. 6,190,912, on Feb. 20, 2001.

STATEMENT OF GOVERNMENT INTEREST

This invention was made in part with funds provided by the United States Government. Accordingly, the United States Government may have certain rights to this invention.

TECHNICAL FIELD

This invention relates generally to pro-apoptotic genes and gene products and, more specifically, to a member of the Bcl-2 gene family.

BACKGROUND OF THE INVENTION

Tissue homeostasis is maintained by the process of apoptosis—that is, the normal physiological process of programmed cell death. Changes to the apoptotic pathway that prevent or delay normal cell turnover can be just as important in the pathogenesis of diseases as are abnormalities in the regulation of the cell cycle. Like cell division, which is controlled through complex interactions between cell cycle regulatory proteins, apoptosis is similarly regulated under normal circumstances by the interaction of gene products that either prevent or induce cell death.

Since apoptosis functions in maintaining tissue homeostasis in a range of physiological processes such as embryonic development, immune cell regulation and normal cellular turnover, the dysfunction or loss of regulated apoptosis can lead to a variety of pathological disease states. For example, the loss of apoptosis can lead to the pathological accumulation of self-reactive lymphocytes that occurs with many autoimmune diseases. Inappropriate loss or inhibition of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can alter the natural progression of many of these diseases.

Although apoptosis is mediated by diverse signals and complex interactions of cellular gene products, the results of these interactions ultimately feed into a cell death pathway that is evolutionarily conserved between humans and invertebrates. The pathway, itself, is a cascade of proteolytic events analogous to that of the blood coagulation cascade.

Several gene families and products that modulate the apoptotic process have now been identified. One family is the Bcl-2 family. Bcl-2 is the first recognized component of programmed cell death or apoptosis (Tsujimoto et al., *Science* 228: 1440–1443, 1985; Nunez, et al., *J. Immunol.* 144: 3602–3610, 1990), an evolutionary conserved process essential for normal development of multicellular organisms and in maintaining tissue homeostasis. Various aspects of involvement of Bcl-2 in this process have been well documented at the molecular and physiological levels (for review see Reed, *Nature* 387: 773, 1997). Bcl-2 is a multifunctional 239 amino acid protein that has a hydrophobic C-terminal membrane anchor preceded by three domains designated BH1, BH2 and BH3 (Bcl-2 Homology domains 1, 2 and 3) that are necessary for its function. Bcl-2 and its homologue Bcl-xL are death antagonists that associate mainly with the outer mitochondrial membrane, the endoplasmic reticulum, and nuclear envelope and moreover, have documented ion channel activity (Reed, *Nature* 387: 773, 1997). These proteins may prevent apoptosis by regulating the electrical and osmotic homeostasis of the mitochondria, a process that is required to prevent mitochondrial swelling, outer membrane rupture and cytochrome c release (Vander Heiden et al., *Cell* 91: 627–637, 1997). Cytochrome c release from the mitochondria is believed to trigger activation of the death caspase cascade, through formation of the Apaf-1/caspase-9/cytochrome c complex (Li et al., *Cell* 91: 479–489, 1997; Reed, *Cell* 91: 559–562, 1997).

Intriguingly, among the members of the Bcl-2 family of proteins discovered in recent years there are death agonists (e.g. Bax, Bad, Bik, Bak, Bid and Hrk). Except for Bad whose BH3 domain is within the putative BH1 domain, all of these proteins contain an independent BH3 domain (Zha, et al., *J. Biol. Chem.* 272: 24101–24104, 1997). It appears that only the BH3 domain is required for their pro-apoptotic activity (Wang, et al., *Genes Dev.* 10: 2859–2869, 1996; Inohara, et al., *EMBO J.* 16: 1686–1694, 1997; Zha, et al., *J. Biol. Chem.* 272: 24101–24104, 1997; Chittenden et al., *EMBO J* 14: 5589–5596, 1995; Boyd, et al., *Oncogene* 11: 1921–1928, 1995; Zha, et al., *J. Biol. Chem.* 271: 7440–7444, 1997; Hunter and Parslow, *J. Biol. Chem.* 271: 8521–8524, 1996; Sattler, et al., *Science* 275: 1129–1132, 1997). This domain interacts with a hydrophobic cleft formed by the BH1, BH2 and BH3 domains of the anti-apoptotic Bcl-xL and Bcl-2 as evident from mutational and structural studies (Sattler, et al., Id,). Interestingly, Bik, Bid and Hrk, which contain only a BH3 domain, seem more potent death effectors than those proteins with all three domains (Bax and Bak) (see Wang, et al., *Genes Dev.* 10: 2859–2869, 1996).

Therefore, there exists a need in the art for methods of assaying compounds for their ability to affect binding activity of the pro-apoptotic with the anti-apoptotic Bcl-2 family members as well as for methods of regulating these proteins in order to treat diseases and syndromes. The present invention provides recombinant Blk constructs that are active in cells, allowing the regulation of apoptosis for the treatment of pathology as well as providing methods and compositions for assaying compounds that inhibit binding of Blk to anti-apoptotic proteins, while further providing other related advantages.

SUMMARY OF THE INVENTION

As noted above, the present invention provides recombinant Blk constructs, mammalian Blk proteins, antibodies that selectively bind to such proteins, and related pharmaceutical compositions and methods. In particular, in one aspect of the invention, nucleic acid molecules encoding mammalian Blk, including human or murine Blk, are provided. Within certain embodiments, the mammalian Blk has the amino acid sequence of SEQ ID No. 2, or a variant thereof, or is encoded by the nucleotide sequence of SEQ ID No. 1 or a variant thereof. In other related aspects, the invention provides a nucleotide sequence encoding a BH3 domain of a mammalian Blk protein. In one embodiment, the BH3 domain has the amino acid sequence Ala Leu Arg Leu Ala Cys Ile Gly Asp Glu Met Asp (SEQ ID NO:3), optionally including one or more amino acid substitutions.

Nucleic acid vectors comprising such Blk sequences and host cells containing such vectors are also provided.

Within another aspect of the invention, isolated mammalian Blk proteins, as well as an isolated BH3 domain of a mammalian Blk protein, are provided. Within a related aspect, antibodies that selectively bind to a mammalian Blk protein are disclosed. In one embodiment, the antibody inhibits the binding of Blk to either Bcl-2 or Bcl-xL. The antibodies provided herein include antibody fragments, single chain antibodies, and humanized antibodies.

Within still other aspects of the subject invention, pharmaceutical compositions comprising the mammalian Blk proteins and gene delivery vehicles comprising nucleic acid molecules as described above are provided.

Within other aspects, methods for treating unwanted cell proliferation through the use of effector molecules that increase unbound Blk protein in a cell are provided. Within certain embodiments, the effector molecule is a peptide that comprises residues 52 to 63 of SEQ ID No. 2 or a variant thereof, wherein the variant has one of more amino acid substitutions at a residue other than Leu55, Gly59 or Asp60. Gene delivery vehicles containing a nucleic acid molecule encoding such a peptide may also be used.

Within a related aspect, methods are provided for screening for such effector molecules, comprising contacting a candidate effector molecule with a solution comprising Blk and Bcl-2 or Bcl-xL; and detecting unbound Blk, wherein an increase in the amount of unbound Blk in the presence of the candidate effector molecule (as compared to the absence of the molecule) indicates that the candidate molecule is suitable for treating unwanted cell proliferation through increasing unbound Blk protein.

These and other aspects of the present invention will become evident upon reference to the following detailed description and attached drawings. In addition, various references that are set forth below describe in more detail certain procedures or compositions and are therefore incorporated by reference in their entirety.

BRIEF DESCRIPTION OF THE DRAWINGS

FIGS. 1A & 1B present the nucleotide and predicted amino acid sequences of an exemplary Blk gene.

FIGS. 3A–F show the subcellular localization of Blk. MCF-7 cells are transfected with a GFP-Blk expression vector (D–F) or a GFP control vector (A–C), and incubated for 16 h at 37° C. The transfected cells are fixed and then stained with the mitochondrial specific stain MitoTracker™ Red CMXRos (Molecular Probes, Inc.). Cells are visualized by confocal laser scanning microscopy. (A–C) Same field of GFP control cells visualized by green florescence (A), MitoTracker$^a$ Red CMXRos (B) or both (C). (D–F) Same field of GFP-Blk cells visualized by green florescence (D), MitoTracker™ Red CMXRos (E) or both (F).

DETAILED DESCRIPTION OF THE INVENTION

Figure 2B:
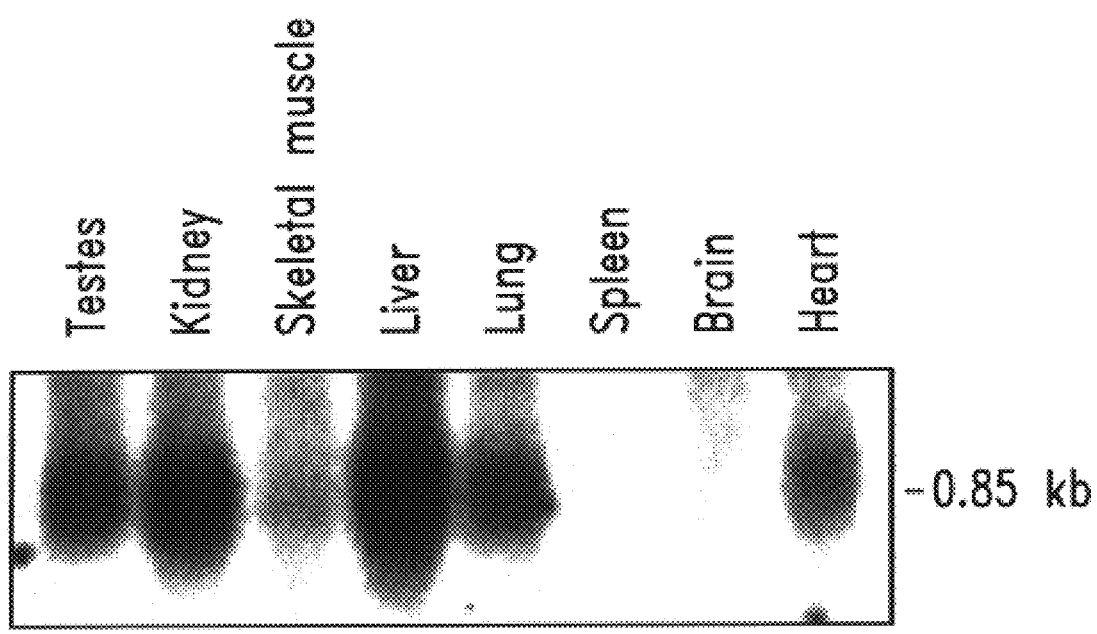
FIGS. 2A and B present an amino acid sequence and tissue distribution of Blk. (A) Alignment of murine Blk (SEQ ID NO:2) and human Bik protein sequences (SEQ ID NO:5). Identical residues are boxed. The 12 amino acid BH3 domain is boxed and shaded. Asterisks indicate residues that are absolutely conserved in the BH3 domains of all mammalian Bcl-2 family members. (B) Northern blot analysis of the expression of murine Blk in adult mouse tissues. The Blk mRNA was detected with a Blk-specific radiolabeled riboprobe. The size of the Blk mRNA in kilobases (0.85 kb) is indicated to the right.

As noted above, the present invention provides Blk genes, Blk gene products and effector molecules that perturb Blk-mediated apoptosis. Murine Blk, which has 43% homology with the human Bik/Nbk (Boyd, et al., *Oncogene* 11: 1921–1928, 1995; Han, et al., *Mol. Cell. Biol.* 16: 5857–5864, 1996), contains a well conserved BH3 domain, binds human Bcl-2 and Bcl-xL and appears to be a potent death agonist.

A. BLK Genes

As noted above, the invention provides compositions relating to pro-apoptotic Bcl-2 family member genes and gene products, and methods for the use of the genes and gene products. In particular, the invention provides Blk genes and proteins. Given the disclosure provided herein, a Blk gene can be isolated from a variety of cell types and engineered to produce a Blk protein.

As used herein, an "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

The present invention, as described herein, provides Blk genes. The nucleotide sequence and predicted amino acid sequence of one exemplary Brk gene is presented in FIG. 1. Blk genes may be isolated from a variety of nucleic acids and typically is isolated from either genomic DNA or preferably cDNA. Generally, the first step in isolation of a Blk gene from genomic DNA or cDNA is generating an appropriate DNA library using techniques known in the art (see Sambrook et al., *Molecular Cloning: A Laboratory Manual,* Cold Spring Harbor Press, 1989) or purchased from commercial sources (e.g., Clontech, Palo Alto, Calif.). Briefly, cDNA libraries can be constructed in bacteriophage vectors (e.g.,λZAPII), plasmid vectors, or other vectors that are suitable for screening, while genomic DNA libraries can be constructed in chromosomal vectors, such as YACs (yeast artificial chromosomes), bacteriophage vectors, such as λEMBL3, λgt10, cosmids, plasmids or the like.

In one embodiment, known Blk nucleic acid sequences may be utilized to design an oligonucleotide hybridization probe suitable for screening genomic or cDNA libraries. Preferably, such oligonucleotide probes are 20–30 bases in length. To facilitate hybridization detection, the oligonucleotide may be conveniently labeled, generally at the 5' end, with a reporter molecule, such as a radionuclide, (e.g., $^{32}$P), enzymatic label, protein label, fluorescent label, or biotin. Such libraries are then generally plated as phage or colonies, depending upon the vector used. Subsequently, a nitrocellulose or nylon membrane, to which the colonies or phage have been transferred, is probed to identify candidate clones that contain a Blk gene. Such candidates may be verified by any of various means including, for example, DNA sequence analysis or hybridization with a second, non-overlapping probe.

Once a library is identified as containing a Blk gene, the gene can be isolated by amplification. Briefly, when using cDNA library DNA as a template amplification primers are designed based upon Blk gene sequences provided herein. Amplification of cDNA libraries made from cells with high Blk activity is preferred. Primers for amplification are preferably derived from sequences in the 5' and 3' untranslated region in order to isolate a full-length cDNA. The primers preferably have a GC content of about 50% and contain restriction sites to facilitate cloning and do not have self-complementary sequences nor do they contain complementary sequences at their 3' end (to prevent primer-dimer formation). The primers are annealed to cDNA or genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis or indirectly through amino acid sequencing of the encoded protein.

Other methods may also be used to obtain a Blk-encoding nucleic acid molecule. For example, such a nucleic acid molecule may be obtained from an expression library by screening with an antibody or antibodies reactive to Blk (see, Sambrook, et al. *Molecular Cloning: A Laboratory Manual,* 2nd Ed., Cold Spring Harbor Laboratory Press, NY, 1987; Ausubel, et al. *Current Protocols in Molecular Biology,* Greene Publishing Associates and Wiley-Interscience, NY, 1995).

Blk genes from a variety of species may be isolated using the compositions provided herein. For closely related species, the murine or human sequence or portion thereof may be utilized as a probe on a genomic or cDNA library. For example, a fragment of Blk that encompasses the BH 3 domain may be labeled and used as a probe on a library constructed from mouse, primate, rat, dog, or other vertebrate, warm-blooded or mammalian species. An initial hybridization at normal stringency (e.g., 5×SSPE at 65° C. or equivalent conditions) may yield candidate clones or fragments. If no hybridization is initially observed, varying degrees of stringency may be used (see Sambrook et al. supra, and other well-known sources for stringency conditions). While such probes may also be used to probe libraries from evolutionarily diverse species, such as Drosophila, hybridization conditions will likely be more relaxed.

While relaxed hybridization conditions using probes designed from mouse or human sequences may identify Blk genes of evolutionarily diverse species it may be more beneficial to attempt to directly isolate these genes from a library using methods which do not require the mouse or human sequence per se. These methods include, but are not limited to, amplification using primers derived from conserved areas (e.g., BH 3 domain), amplification using degenerate primers from various regions, antibody probing of expression libraries, and the like. For example, random-primed amplification (e.g., polymerase chain reaction) may be employed (see, e.g., *Methods Enzymol.* 254: 275, 1995; *Trends Genet.* 11: 242, 1995; Liang and Pardee, *Science* 257: 967, 1992; Welsh et al., *Nucl. Acids Res.* 20: 4965, 1992). In addition, variations of random-primed PCR may also be used, especially when a particular gene or gene family is desired. In such a method, one of the amplification primers is an "anchored oligo(dT) (oligo(dT)dN)" and the other primer is a degenerate primer based upon amino acid or nucleotide sequence of a related gene. A gene sequence is identified as a Blk by amino acid similarity and/or nucleic acid similarity. Generally, amino acid similarity is preferred. Candidate Blk genes are examined for enzyme activity by one of the functional assays described herein or other equivalent assays.

As will be appreciated by those skilled in the art, a nucleotide sequence encoding a Blk protein may differ from the known native sequences, due to codon degeneracies, nucleotide polymorphisms, or amino acid differences. In other embodiments, variants should preferably hybridize to the native nucleotide sequence at conditions of normal stringency, which is approximately 25–30° C. below Tm of the native duplex (e.g., 5×SSPE, 0.5% SDS, 5× Denhardt's solution, 50% formamide, at 42° C. or equivalent conditions; see generally, Sambrook et al. *Molecular Cloning: A Laboratory Manual,* 2nd ed., Cold Spring Harbor Press, 1987; Ausubel et al., *Current Protocols in Molecular Biology,* Greene Publishing, 1987). Low stringency hybridizations utilize conditions approximately 40° C. below Tm, and high stringency hybridizations utilize conditions approximately 10° C. below Tm. Variants preferably have at least 75% nucleotide identity to native sequence, preferably at least 80%, 85%, and most preferably at least 90% nucleotide identity.

Furthermore, variants of Blk genes provided herein may be engineered from natural variants (e.g., polymorphisms, splice variants, mutants), synthesized or constructed. Many methods have been developed for generating mutants (see, generally, Sambrook et al., supra; Ausubel, et al., supra, and the discussion above). Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically $E.$ $coli,$ but alternatively, other prokaryotes, yeast or other eukaryotes. Standard screening and vector growth protocols are used to identify mutant sequences and obtain high yields.

Similarly, deletions and/or insertions of Blk genes may be constructed by any of a variety of known methods as discussed supra. For example, the gene can be digested with restriction enzymes and religated such that a sequence is deleted or religated with additional sequences such that an insertion or large substitution is made. Other means of generating variant sequences may be employed with methods known in the art, for example those described in Sambrook et at. (supra) and Ausubel et al. (supra). Verification of variant sequences is typically accomplished by restriction enzyme mapping, sequence analysis, or probe hybridization. Variants that heterodimerize with Bcl-2 or Bcl-XL are useful in the context of this invention.

The nucleic acid molecule encoding Blk may be fused to a molecule encoding a different protein. As will be appreciated, either gene may have its entire coding region or only part of its coding region. Thus, it may be desireable to use only the BH3 domain of Blk. The choice of the fusion partner depends in part upon the desired application. The fusion partner may be used to alter specificity of Blk, provide a reporter function, provide a tag sequence for identification or purification protocols, and the like. The reporter or tag can be any protein that allows convenient and sensitive measurement and does not interfere with the function of Blk. For reporter function, green fluorescent protein and β-galactosidase are readily available as DNA sequences. A peptide tag is a short sequence, usually derived from a native protein, which is recognized by an antibody or other molecule. Such peptide tags include FLAG®, Glu-Glu tag (Chiron Corp., Emeryville, Calif.) KT3 tag (Chiron Corp.), T7 gene 10 tag (Invitrogen, La Jolla, Calif.), T7 major capsid protein tag (Novagen, Madison, Wis.), and HSV tag (Novagen). Besides tags, other types of proteins or peptides, such as glutathione-S-transferase may be used.

In addition, portions or fragments of Blk gene may be isolated or constructed. For example, the BH3 domain (amino acids 52–63) may be synthesized or isolated by well known techniques from a DNA source containing these nucleic acids. A convenient means for obtaining fragments is either by synthesis or restriction enzyme digestion and insertion into a vector (e.g., plasmid) that can readily be propagated.

B. BLK Gene Products

As noted above, the present invention provides gene products of the Blk gene as well as peptides derived from Blk. The proteins and peptides can be used in assays for inhibitors of Blk binding to Bcl-2 family members, therapeutically in the treatment of diseases and disorders, as immunogens for raising antibodies, and the like.

Within the context of this invention, it should be understood that a Blk includes wild-type protein sequences, as well as other variants (including alleles) of the native protein sequence. Briefly, such variants may result from natural polymorphisms or may be synthesized by recombinant methodology, and differ from wild-type protein by one or more amino acid substitutions, insertions, deletions, or the like. Typically, when engineered, amino acid substitutions will be conservative, i.e., substitution of amino acids within groups of polar, non-polar, aromatic, charged, etc. amino acids. In the region of homology to the native sequence, variants should preferably have at least 90% amino acid sequence identity, and within certain embodiments, greater than 92%, 95%, or 97% identity. In order to maintain the binding function of Blk to Bcl-2 and Bcl-xL, conserved residues in the BH3 domain that are critical to binding are preferably not altered. These residues include Leu55, Gly59, and Asp60.

1. Vectors, Host Cells and Means of Expressing Protein

Blk may be expressed in a variety of host organisms. In certain embodiments, Blk is produced in bacteria, such as $E.$ $coli,$ or in mammalian cells (e.g., CHO and COS-7), for which many expression vectors have been developed and are available. Other suitable host organisms include other bacterial species, and eukaryotes, such as yeast (e.g., *Saccharomyces cerevisiae*), and insect cells (e.g., Sf9).

A DNA sequence encoding Blk is introduced into an expression vector appropriate for the host. In certain embodiments, Blk is inserted into a vector such that a fusion protein is produced. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At minimum, the vector must contain a promoter sequence. As used herein, a "promoter" refers to a nucleotide sequence that contains elements that direct the transcription of a linked gene. At minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked".

Other regulatory sequences may be included. Such sequences include a transcription termination signal sequence, secretion signal sequence, origin of replication, selectable marker, and the like. The regulatory sequences are operationally associated with one another to allow transcription or translation.

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009) and the like.

The promoter controlling transcription of Blk may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the *E. coli* lacI repressor responsive to IPTG induction, the temperature sensitive λcI857 repressor, and the like. The *E. coli* lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in the host cells. Thus, when the host cell is a bacterium, the vector preferably contains a bacterial origin of replication. Preferred bacterial origins of replication include the f1-ori and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk–hosts). However, drug markers are also available (e.g., G418 resistance and hygromycin resistance).

The sequence of nucleotides encoding Blk may also include a secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184:99–105, 1985). Prokaryotic and eukaryotic secretion signals that are functional in *E. coli* (or other host) may be employed. The presently preferred secretion signals include, but are not limited to, those encoded by the following *E. coli* genes: pelB (Lei et al., *J. Bacteriol.* 169:4379, 1987), phoA, ompA, ompT, ompF, ompC, beta-lactamase, and alkaline phosphatase.

One skilled in the art appreciates that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ 18 (Amersham International plc, England), pACYC 177, pGEX series, and the like are suitable for expression of a Blk. Baculovirus vectors, such as pBlueBac (see, e.g., U.S. Pat. Nos. 5,278, 050, 5,244,805, 5,243,041, 5,242,687, 5,266,317, 4,745,051, and 5,169,784; available from Invitrogen, San Diego) may be used for expression in insect cells, such as *Spodoptera frugiperda* sf9 cells (see, U.S. Pat. No. 4,745,051). The choice of a bacterial host for the expression of a Blk is dictated in part by the vector. Commercially available vectors are paired with suitable hosts.

A wide variety of suitable vectors for expression in eukaryotic cells are available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, Blk gene is cloned into a gene targeting vector, such as pMC1neo, a pOG series vector (Stratagene Cloning Systems).

2. Isolation of Blk Gene Products

Blk protein is isolated by standard methods, such as affinity chromatography, size exclusion chromatography, metal ion chromatography, ionic exchange chromatography, HPLC, and other known protein isolation methods. (see generally Ausubel et al. supra; Sambrook et al. supra). An isolated purified protein gives a single band on SDS-PAGE when stained with Coomassie blue.

Blk may be expressed as a hexa-his fusion protein and isolated by metal-containing chromatography, such as nickel-coupled beads. Briefly, a sequence encoding His$_6$ is linked to a DNA sequence encoding a Blk. Although the His$_6$ sequence can be positioned anywhere in the molecule, preferably it is linked at the 3' end immediately preceding the termination codon. The fusion may be constructed by any of a variety of methods. A convenient method is amplification of the Blk gene using a downstream primer that contains the codons for His$_6$.

Purified Blk protein may be used in assays to screen for inhibitory drugs. These assays may be performed in vitro or in vivo and utilize any of the methods described herein or that are known in the art. The protein may also be crystallized and subjected to X-ray analysis to determine its 3-dimensional structure or used to raise antibodies.

3 Blk Peptides

Peptides may be synthesized by standard chemical methods, including synthesis by automated procedure. In one procedure, peptide analogues are synthesized based on the standard solid-phase Fmoc protection strategy with HATU as the coupling agent. The peptide is cleaved from the solid-phase resin with trifluoroacetic acid containing appropriate scavengers, which also deprotects side chain functional groups. It will be appreciated that other automated and manual methods for synthesizing peptides are known in the art. For example, the tBoc protection strategy, or use of different coupling reagents or the like can be employed to produce equivalent peptides.

Crude peptide may be purified using preparative reversed-phase chromatography. Other purification methods, such as partition chromatography, gel filtration, gel electrophoresis, or ion-exchange chromatography may be used.

C. Effectors of Blk-Mediated Apoptosis

As discussed above, Blk is a potent death agonist. Its pro-apoptotic activity can be counteracted by co-expression of Bcl-2 or Bcl-xL, most likely through binding of Blk to those proteins, thus rendering Blk unavailable. As such, an effector molecule may act to increase or decrease Blk-mediated apoptosis.

The effector may act by preventing expression of Blk, by preventing binding of Blk to partner proteins, by causing dissociation of the bound proteins, or by some other mechanism. Furthermore, the effector may act directly or indirectly. In preferred embodiments, effectors interfere in the binding of Blk protein to either Bcl-2 or Bcl-xL. Effectors may also interfere with Blk homodimer formation. In other preferred embodiments, the effectors are small molecules. Effectors should have a minimum of side effects and are preferably non-toxic. Effectors that can penetrate cells are preferred.

Candidate effectors may be isolated or procured from a variety of sources, such as bacteria, fungi, plants, parasites, libraries of chemicals, random peptides or the like. Candidate effectors may also be variants of Blk, peptides or variant peptides of Blk, antisense to nucleic acids encoding Blk, inhibitors of promoter activity of Blk, and the like. Effectors may be also be rationally designed, based on the protein structure determined from X-ray crystallography (see, Livnah et al., *Science* 273: 464, 1996).

1. Antisense

Another effector of the present invention is antisense RNA or DNA to Blk coding sequence. Antisense nucleic acids directed to a particular mRNA molecule have been shown to inhibit protein expression of the encoded protein. Based upon the Blk coding sequence presented herein, an antisense sequence is designed and preferably inserted into a vector suitable for transfection into host cells and expression of the antisense. The antisense nucleic acids should anneal to Blk mRNA under physiological conditions. Preferably, the antisense does not anneal to other mRNAs, especially those related molecules. Such antisense effectors may be produced by a variety of methods known in the art, including the use of a heterologous expression cassette introduced into cells. Such effectors and methods related thereto are described in detail in *Antisense RNA and DNA*, (1988), D. A. Melton, Ed., Cold Spring Harbor Laboratory, Cold Spring Harbor, N.Y.; U.S. Pat Nos. 5,610,288; 5,665,580; and 5,681,944.

2. Ribozymes

In another preferred embodiment, the effector is a ribozyme. Ribozymes that cleave Blk mRNA are RNA molecules that contain anti-sense sequences for Blk and an RNA-cleaving enzymatic activity that cleaves a specific site in a target RNA. Two types of ribozymes are particularly useful in this invention, the hammerhead ribozyme (Rossi, J. J. et al., *Pharmac. Ther.* 50:245–254, 1991) and the hairpin ribozyme (Hampel et al., *Nucl. Acids Res.* 18:299–304, 1990, and U.S. Pat. No. 5,254,678, issued Oct. 19, 1993). The recognition sequence for the hairpin ribozyme is any RNA sequence consisting of NNNBN*GUCNNNNNNNN (SEQ ID NO:4) (where N*G is the cleavage site, where B is any of G, C, or U, and where N is any of G, U, C, or A), and for the hammerhead ribozyme is any RNA sequence consisting of NUX (where N is any of G, U, C, or A and X represents C, U, or A). The additional nucleotides of the hammerhead ribozyme or hairpin ribozyme are determined by the target flanking nucleotides and the hammerhead consensus sequence (see Ruffner et al., *Biochemistry* 29:10695–10702, 1990). The preparation and use of certain ribozymes is described in Cech et al. (U.S. Pat. No. 4,987,071). Ribozymes are preferably expressed from a vector introduced into the host cells.

3. Antibodies

Antibodies to Blk proteins may readily be prepared given the disclosure provided herein. Such antibodies may specifically recognize wild type Blk protein, a mutein, or a BH3 domain. Antibodies may be used for isolation of the protein, inhibiting activity of the protein (antagonist), or enhancing activity of the protein (agonist). As well, assays for small molecules that interact with Blk will be facilitated by the development of antibodies.

Within the context of the present invention, antibodies are understood to include monoclonal antibodies, polyclonal antibodies, anti-idiotypic antibodies, antibody fragments (e.g., Fab, and F(ab')$_2$, F$_v$, variable regions, or complementarity determining regions). Antibodies are generally accepted as specific to Blk protein if they bind with a K$_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660–672, 1949).

Briefly, a polyclonal antibody preparation may be readily generated in a variety of warm-blooded animals such as rabbits, mice, or rats. Typically, an animal is immunized with Blk or peptide thereof (e.g., BH3 domain), which is preferably conjugated to a carrier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual,* Harlow and Lane (eds.), Cold Spring Harbor Laboratory Press, 1988). Various immortalization techniques, such as mediated by Epstein-Barr virus or fusion to produce a hybridoma, may be used. In a preferred embodiment, immortilization occurs by fusion with a suitable myeloma cell line (e.g, NS-1 (ATCC No. TIB 18), and P3X63 -Ag 8.653 (ATCC No. CRL 1580)) to create a hybridoma that secretes monoclonal antibody. Following selection of hybridomas, the hybridomas may be screened for the presence of antibodies that are reactive against Blk protein. A wide variety of assays may be utilized, including for example countercurrent immunoelectrophoresis, radioimmunoassays, radioimmunoprecipitations, enzyme-linked immunosorbent assays (ELISA), dot blot assays, western blots, immunoprecipitation, inhibition or competition assays, and sandwich assays (see U.S. Pat. Nos. 4,376,110 and 4,486,530; see also *Antibodies. A Laboratory Manual,* Harlow and Lane (eds.), Cold Spring Harbor Laboratory Press, 1988).

Other techniques may also be utilized to construct monoclonal antibodies (see Huse et al., *Science* 246:1275–1281, 1989; Sastry et al., *Proc. Natl. Acad. Sci. USA* 86.5728–5732, 1989; Alting-Mees et al., *Strategies in Molecular Biology* 3:1–9, 1990; describing recombinant techniques). Briefly, mRNA is isolated from a B cell population and utilized to create heavy and light chain immunoglobulin cDNA expression libraries in suitable vectors, such as λImmunoZAP™ H or λImmunoZAP™. These vectors may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. Amplification products are inserted into vectors such as ImmunoZAP™ H or ImmunoZAP™ L (Stratacyte), which are then introduced into *E. coli,* yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, techniques may be utilized to change a "murine" antibody to a "human" antibody, known familiarly as a "humanized" antibody, without altering the binding specificity of the antibody.

Once suitable antibodies have been obtained, they may be isolated or purified by many techniques (e.g., peptide or protein affinity columns, HPLC or RP-HPLC, purification on protein A or protein G columns) well known to those of ordinary skill in the art (see *Antibodies: A Laboratory Manual,* Harlow and Lane (eds.), Cold Spring Harbor Laboratory Press, 1988).

4. Blk Fragments

In other preferred embodiments, the effector is a peptide subfragment of Blk that binds to Bcl-2 and Bcl-xL. For example, a peptide of Blk, such as the BH3 domain that competitively inhibits the binding of Blk to Bcl-2 will increase the amount of free Blk protein and lead to apoptosis. Generally, these peptides have native BH3 domain sequence (residues 52–63 in SEQ ID NO:3; Ala-Leu-Arg-Leu-Ala-Cys-Ile-Gly-Asp-Glu-Met-Asp), but variants may have increased activity. As indicated herein Leu55, Gly59, and Asp60 appear to be required for binding of Blk to Bcl-2 and Bcl-xL. Thus, preferably these residues are not altered. The peptides, however, may have additional residues. Peptides may be constructed by the methods described herein. For effective inhibition, peptide effectors may be expressed from vectors transfected or infected into host cells. Eukaryotic vectors are well known and readily available.

5. Screening Assays

Screening assays for effectors will vary according to the type of effector and nature of the activity that is being altered. Assays include protein binding assays, measurement of apoptosis and the like.

One binding assay that may be used is a yeast 2-hybrid binding system. Briefly, in a two-hybrid system, a fusion of a DNA-binding domain-Blk (or Bcl-2; Bcl-xL) protein (e.g., GAL4-Blk fusion) is constructed and transfected into a cell containing a GAL4 binding site linked to a selectable marker gene. The whole Blk protein or subregions, such as the BH3 domain may be used. A second construct containing the binding partner (e.g., Bcl-2 or Bcl-xL) fused to the GAL4 activation domain is co-transfected. The yeast cells are contacted with candidate effector molecules and the amount of reporter gene expression is measured. An effector that disrupts or prevents binding of Blk with Bcl-2 or Bcl-xL will be evidenced by a decrease in reporter gene expression compared to expression in yeast cells contacted with vehicle alone.

Other assays may also be used to identify interacting proteins. Such assays include ELISA, Western blotting, co-immunoprecipitations and the like. These assays are well known in the art.

Other assays may include cell apoptosis assays. Briefly, cells may be transfected (stably or transiently) with expression constructs containing Blk or functional fragments thereof (e.g. BH3 domain). At various times thereafter apoptosis can be detected in said cells using a variety of methods known to those skilled in the art (see "Apoptosis Techniques and Protocols," Judes Poirier, editor, Humana Press; "Apoptosis: The Molecular Basis of Cell Death," D. Tomei and F. Cope, editors, Cold Spring Harbor Laboratory Press, 1991). The ability of Brk to induce apoptosis and the ability of Blk effectors (e.g., peptides, ribozymes, antisense molecules and the like) to inhibit Brk-induced apoptosis can be monitored in this way.

D. Uses of Blk Genes, Gene Products, and Effector Molecules

The compositions described herein, including Blk genes, gene products and effector molecules have myriad uses. For example, these compositions may be used in diagnostic assays, for screening assays, or as therapeutic agents.

For diagnostics, the detection and quantification of Blk is an indicator of apoptosis. Thus, the detection of the pro-apoptotic Blk would be important in monitoring cell growth or to detect or monitor the course of diseases. Blk can be detected as protein or as nucleic acid using the compositions provided herein. For example, antibody-based assays (e.g., ELISA, cell staining, Western blots) can be used to detect Blk protein. Nucleic acid encoding Blk can be detected in situ by hybridizing antisense Blk to RNA appropriately fixed cell samples. Nucleic acid can also be detected after isolation from cells by standard techniques, such as Northern blotting or amplification.

The association of Blk with Bcl-2 and Bcl-xL can also be the basis of assays for effect of mutations, identification of effector molecules that interfere with or inhibit binding of the proteins. Examples of assays for protein-protein binding are described above.

Blk and the effector molecules described above can be administered to cells in vivo or ex vivo in order to promote or inhibit apoptosis. For example, delivery of Blk protein can increase the levels of Blk in a cell and tip the cell toward apoptosis. As well, delivery of effector molecules that disrupt or interfere with binding of Blk to Bcl-xL or Bcl-2 can increase levels of Blk and thus, promote apoptosis. In contrast, effector molecules that diminish levels of free or unbound Blk, such as antisense, ribozymes, and antibodies, will serve to promote cell growth or survival by inhibiting apoptosis. As discussed below, Blk genes and gene products and effector molecules can be delivered as pharmaceuticals or in a gene delivery vehicle.

Furthermore, the genes described herein can be used to construct transgenic and null mutant animals (e.g., "knockout mice") to facilitate testing of candidate effector molecules. The Blk gene is preferably under control of a tissue-specific promoter for transgenic mice vector constructs.

As noted above, Blk protein or peptide, as well as the various effector molecules may be delivered to cells as part of gene delivery vehicles. In many diseases and syndromes, too little apoptosis is an important feature in their development. Treatment of many autoimmune diseases and tumors would benefit from increased apoptosis. One means to increase apoptosis is to provide target cells with Blk genes in an expressible form. This may be accomplished by delivery of DNA or cDNA capable of in vivo transcription of Blk. More specifically, in order to produce Blk in vivo, a nucleic acid sequence coding for the Blk protein is placed under the control of a eukaryotic promoter (e.g., a pol III promoter, CMV or SV40 promoter). Where it is desired to more specifically control transcription, Blk may be placed under the control of a tissue or cell specific promoter (e.g., to target cells in the liver), or an inducible promoter, such as metallothionein. As will be appreciated by those in the art, similar techniques may be used to introduce vactors encoding antisense, ribozymes, antibodies, and other effector moleucles. Thus, the same principles discussed herein will generally apply to introduction of these other molecules.

Many techniques for introduction of nucleic acids into cells are known. Such methods include retroviral vectors and subsequent retrovirus infection, adenoviral or adeno-associated viral vectors and subsequent infection, and complexes of nucleic acid with a condensing agent (e.g., polylysine). These complexes or viral vectors may be targeted to particular cell types by way of a ligand incorporated into the vehicle. Many ligands specific for tumor cells and other cells are well known in the art.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218.

Within certain aspects of the invention, nucleic acid molecules may be introduced into a host cell utilizing a vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413–7417, 1989), microprojectile bombardment (Williams et al., *PNAS* 88:2726–2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985–16987, 1989), as well as psoralen inactivated viruses such as Sendai or Adenovirus. In one embodiment, the construct is introduced into the host cell using a liposome.

E. Administration

As discussed above, Blk is a potent death agonist, which induces apoptosis. Dysregulated apoptosis is a part of many diseases and disorders, including cancer, autoimmunity, and neurodegenerative disorders. Controlling apoptosis is a way to counteract or treat diseases. Treatment refers to a lessening or amelioration of the disease, symptoms, or other effects of the disease. Patients suitable for treatment with the compositions described herein are identified by well known hallmarks of the particular diseases.

As noted above, pharmaceutical compositions also are provided by this invention. These compositions may contain any of the above described effectors, DNA molecules, vectors or host cells, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intrahepatically, intramuscularly, intraocularly, intraperitoneally, intrathecally, intravenously, subcutaneously or even directly into a tumor. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. Pharmaceutical compositions are useful for both diagnostic or therapeutic purposes.

The compositions may be administered in a delivery vehicle. For example, the composition can be encapsulated in a liposome (see, e.g., WO 96/10585; WO 95/35094), complexed with lipids, encapsulated in slow-release or sustained release vehicles, such as poly-galactide, and the like. Within other embodiments, compositions may be prepared as a lyophilizate, utilizing appropriate excipients to provide stability.

The level of therapeutic in serum and other tissues after administration can be monitored my various well-established techniques such as chromatographic or antibody based, such as ELISA, assays.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

Isolation of Blk cDNA

To identify additional members of the BH3-only gene family that are involved in apoptosis, GenBank EST data base is scanned for sequences that encode a conserved BH3 domain. One EST fragment, GenBank Accession No. 694727, is identified as encoding BH3 sequence. Using this EST sequence, an amplification primer corresponding to the 3' region is designed as an anti-sense primer, and a vector specific primer (gt 11 forward or reverse) is designed as a sense primer.

Using these primers, a Blk cDNA is amplified from a mouse 14.5 day embryo λgt11 cDNA library that is constructed from random primed mRNA. The clone encodes a new bik-related protein of 150 amino acids (FIG. 2A). This protein has approximately 43% amino acid identity with human Bik and has a fully conserved BH3 domain of 12 amino acids (FIG. 2A) that is also present in other Bcl-2 family members. The two proteins, however, are less conserved in the regions flanking the BH3 domain. Blk also has five "deletions" making it 10 amino acids shorter than Bik. Based on these criteria and its apoptotic activity (see below) the new protein is designated Bik-like killer (Blk).

Example 2

Properties of Blk Gene and Gene Product

Tissue Expression of Blk mRNA—The tissue distribution of Blk is examined in various mouse tissue mRNA samples by Northern blot analysis. Blk riboprobe was synthesized by in vitro transcription of a full length Blk cDNA in pBluescript Ks⁻ vector (Stratagene) using RNA polymerase in the presence of $\alpha$-$^{32}$-P-CTP. This probe was hybridized to a mouse mRNA blot obtained from Clontech.

As shown in FIG. 2B, the Blk riboprobe detects a ~0.85-kilobase transcript in testes, kidney, liver, lung and heart, but not in skeletal muscle, spleen and brain. The highest expression is seen in liver and kidney. This restricted expression differs from that observed with human Bik, which is widely expressed in both adult tissues and established cell lines (Boyd et al., *Oncogene* 11: 1921, 1995), but is more similar to the mRNA expression of murine Bid, another BH3 only apoptotic protein, which is relatively abundant in brain and spleen tissues (Wang et al., *Genes Dev.* 10: 2859, 1996).

Localization of Brk to the mitochondrial membrane. A characteristic feature of members of the Bcl-2 family is the presence of a C-terminal hydrophobic transmembrane domain, which may be responsible for the association of these proteins with subcellular membranes such as the outer mitochondrial, endoplasmic and perinuclear membranes. Blk possesses such a domain at its C-terminus (residues 130–149) (FIG. 2A). This and its ability to interact with Bcl-2 and Bcl-xL (see below) suggest that it could also associate with these subcellular membranes.

To examine this possibility, Brk is expressed in MCF-7 cells as a fusion protein with green fluorescence protein (GFP) in the expression vector pEGFP-C1 (Clontech). Cells are harvested and fixed 16 h post-transfection, before apoptosis is induced. Fixed cells are fixed, stained with the mitochondrial specific stain MitoTracker$^a$ Red and examined for GFP expression by confocal laser scanning microscopy (FIG. 3). Unlike the GFP non-fusion protein (FIGS. 3A–C), the GFP-Blk fusion protein exhibits a punctate florescence that colocalizes with the MitoTracker$^a$ Red stain (FIG. 3D–F), suggesting that Blk is predominantly associated with mitochondrial membranes.

Apoptotic activity of Blk. The pro-apoptotic proteins of the Bcl-2 family (e.g. Bax) are believed to initiate the apoptotic process stoichiometrically, where the death or survival of the cell depends upon the ratio of the apoptotic to the anti-apoptotic proteins in the cell. To examine the apoptotic activity of Blk compared to Bik and Bax, increasing amounts of constructs expressing these proteins are transfected into MCF-7 cells and the number of apoptotic cells are scored.

For apoptosis assays, pRSC-LacZ (Srinivasula et al., *J. Biol. Chem.* 272: 18542, 1997) is used. In this vector, the Bcl-2 family genes (Blk, Bik, Bax and Blk BH3 mutants) are expressed under control of the CMV promoter and lacZ is expressed under control of the Rous Sarcoma virus (RSV) promoter. To assay for apoptosis, MCF-7 or 293 cells were transfected with the pRSC-LacZ constructs in the presence or absence of different apoptosis-inhibitors. The cells were stained with β-galactosidase 30 h after transfection and examined for morphological signs of apoptosis. The percentage of round blue apoptotic cells (mean±SD) were represented as a function of total blue cells under each condition (n>3).

Figure 4A:
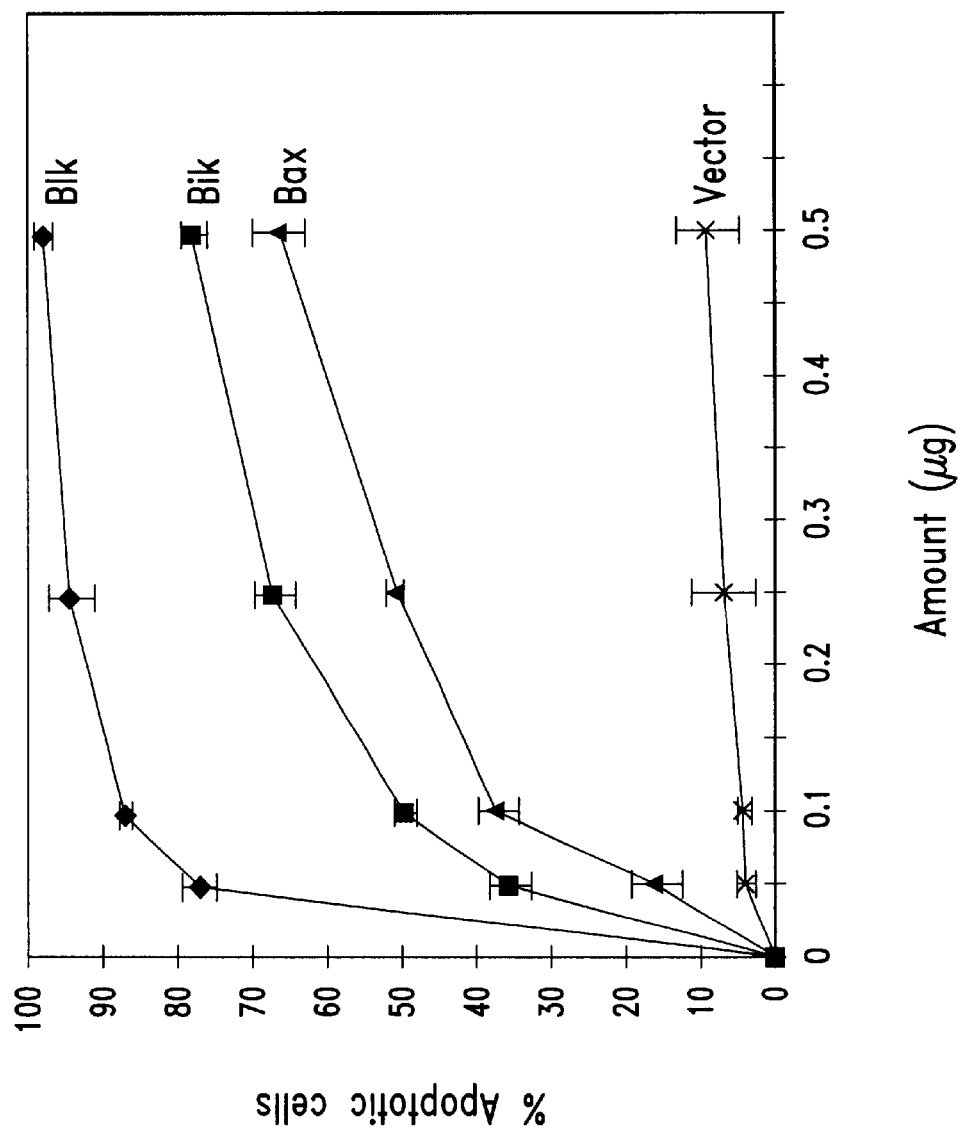
FIGS. 4A–C present graphs showing that the expression of Blk induces apoptosis that is inhibited by Bcl-2 and Bcl-xL. (A) Comparative effect of Blk, Bik and Bax expression on MCF-7 cells. MCF-7 cells are transfected with increasing amounts of pRSC-LacZ vectors expressing Blk, Bik or Bax, or empty pRSC-LacZ vector. 30 h after transfection cells are stained with β-galactosidase and examined for morphological signs of apoptosis. The graphs show the percentage of round blue apoptotic cells (mean±SD) as a function of total blue cells under each condition ($n^3$ 3). (B) Bcl-2 and Bcl-xL inhibit Blk-, Bik- and Bax-induced apoptosis. MCF-7 cells are transfected with 0.5 μg of the indicated expression constructs in combination with 2 μg of Bcl-2 or Bcl-xL constructs and then assayed for apoptosis as in A. (C) Concentration-dependent inhibition of Brk-induced apoptosis by Bcl-2 and Bcl-xL. MCF-7 cells are transfected with increasing ratios of Bcl-2 or Bcl-xL to Blk (0.25 μg in each case) or empty vector (0.25 μg) and then assayed for apoptosis as in A.

Consistent with previous observations, the three proteins induce apoptosis in a concentration dependent manner, where the apoptotic effect is dependent on the amount of DNA transfected (FIG. 4A). Interestingly, in all experiments, murine Brk shows higher potency than Bik and Bax. Similar results are observed in the human embryonic kidney 293 cells.

Figure 4B:
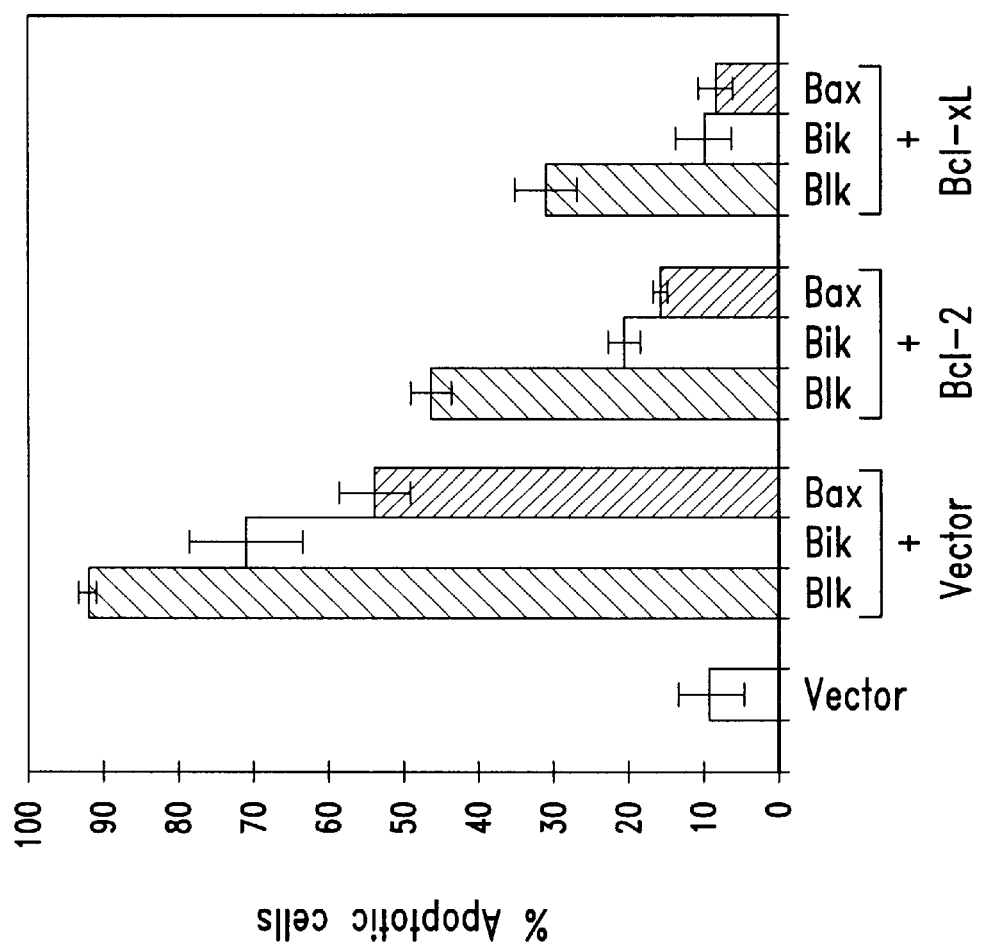
Figure 4C:
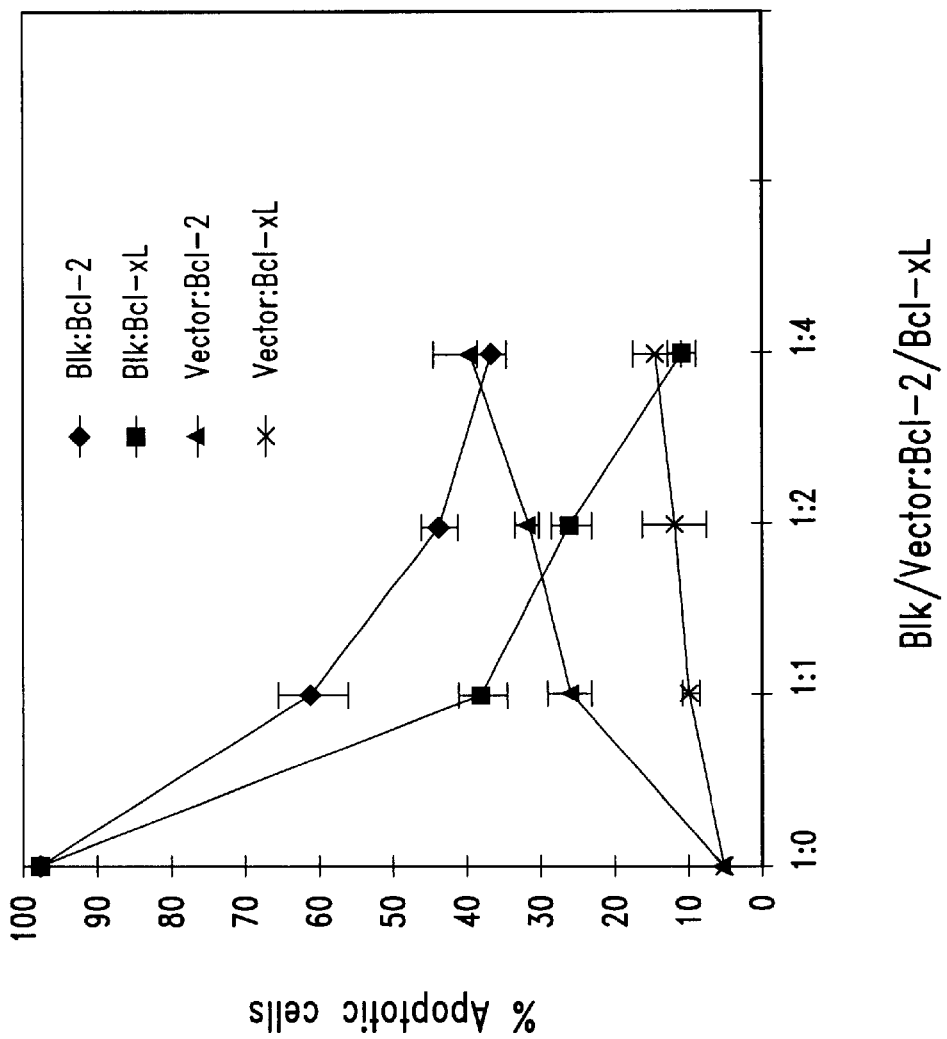

Also consistent with their ability to antagonize the death promoting activity of the pro-apoptotic Bcl-2 family members, transfected Bcl-2 and Bcl-xL are able to suppress the pro-apoptotic activity of Blk, Bik and Bax (FIG. 4B). In all, Bcl-xL is a better inhibitor of apoptosis than Bcl-2. The extent of Bcl-2/Bcl-xL-mediated inhibition of apoptosis induced by the three death agonists follows the order Blk<Bik<Bax. This correlates with the ability of Blk to induce more apoptosis than Bik and Bax (FIG. 4A). In addition, the inhibition of apoptosis depends on the ratio of Bcl-2 or Bcl-xL to Blk, as increasing this ratio results in more inhibition of apoptosis (FIG. 4C). These data support earlier observations that the ratio of the pro- to the anti-apoptotic Bcl-2 proteins determines whether cells die or survive. Thus, Brk is a potent death effector, and its apoptotic activity is inhibited in the presence of co-expressed Bcl-2 or Bcl-xL.

Example 3

Interaction of BLK Gene Product with BCL-2 and BCL-XL

Blk binds Bcl-2 and Bcl-xL. All the proapoptotic Bcl-2 family members can heterodimerize with Bcl-2 and Bcl-xL. To determine whether Blk can also bind to Bcl-2 or Bcl-xL, in vivo and in vitro binding studies are performed. Bcl-2 and Bcl-xL are constructed as GST fusion proteins inpGEX-4T-2 and pGEX-2T, respectively, by placing the coding sequence of Bcl-2 or Bcl-XL in frame C-terminal to the GST protein (Pharmacia). GST fusion proteins are expressed in *E. coli* and purified by affinity chromatography on a glutathione-coupled substrateGlutathione Sepharose 4B (Pharmacia). $^{35}$S-labeled (Blk, Bik, Bax) proteins are expressed in vitro using a coupled transcription/translation system in rabbit reticulocyte lysate (TNT Kit; Promega). In vitro protein-protein interactions are carried out according to Boyd et. al. (supra). Briefly, labeled proteins are precleared by mixing with glutathione-coupled Sepharose beads, which are then removed by centrifugation. The supernatants are incubated with GST-Bcl-2, GST-Bcl-xL or GST immobilized on glutathione-coupled Sepharose beads for 2 h at 4° C. After extensive washing, proteins are recovered by boiling the beads in SDS-sample buffer and analyzed on 12% SDS-PAGE.

For in vivo studies, the proteins are tagged with either FLAG- or T7-epitope by cloning amplified cDNAs of the respective genes into pFLAG CMV-2 (Kodak) and pcDNA-3-T7 (Invitrogen) vectors, respectively. For in vivo interaction studies of T7-tagged Bcl-2 and Bcl-xL with FLAG-tagged Blk, Bik and Bax, the corresponding proteins are co-expressed in human embryonic kidney 293 cells, and interacting proteins aere isolated by immunoprecipitation with anti-Flag monoclonal antibody, followed by immunoblot analysis with an HRP-conjugated T7-antibody as described before (Srinivasula, et al., supra).

Figure 5A:
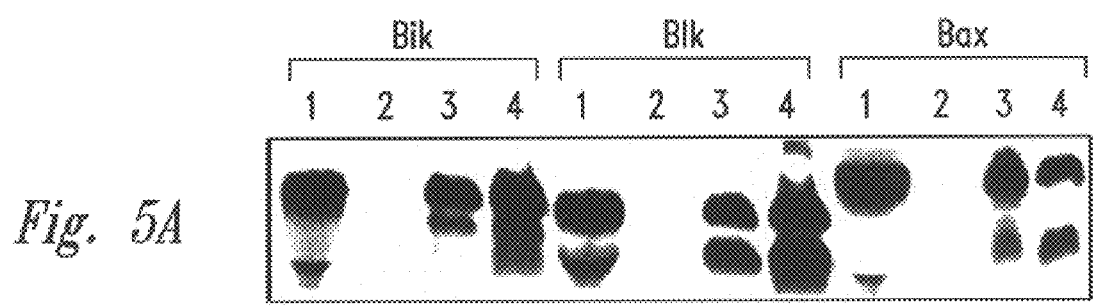
FIGS. 5A–D demonstrates that Blk interacts directly with Bcl-2 and Bcl-xL. (A) In vitro interaction of Bik, Blk or Bax with GST-Bcl-2 or GST-Bcl-xL. 35S-labeled Bik, Brk or Bax (lane 1, input) are precipitated with GST (lane 2), GST-Bcl-2 (lane 3), or GST-Bcl-xL (lane 4) and then analyzed by SDS-PAGE and autoradiography. (B) In vivo interaction of Bik, Blk and Bax with co-expressed Bcl-2 or Bcl-xL. 293 cells are transfected with expression plasmids encoding T7-epitope tagged Bcl-2 or Bcl-xL and Flag-epitope tagged Bik, Blk or Bax. After 36 h, extracts are prepared and immunoprecipitated with a monoclonal antibody to the Flag-epitope. The immunoprecipitates (upper panel) and the corresponding cellular lysates (lower panel) are analyzed by SDS-PAGE and immunoblotted with a HRP-conjugated T7-antibody. IP, immunoprecipitates. (C) Mutations in the BH3 domain of Blk abrogate its ability to interact with Bcl-2 and Bcl-xL. 35S-labeled wild type Blk, mutant Blk-DG59 (M1) or mutant Blk-DG59-D60 (M2) (lane 1, input) are precipitated with GST (lane 2), GST-Bcl-2 (lane 3), or GST-Bcl-xL (lane 4) and then analyzed by SDS-PAGE and Coomassie staining to detect the GST fusion proteins (lower panel) and autoradiography to detect the interacting labeled proteins (upper panel). (D) Mutations in the BH3 domain of Blk abrogate its proapoptotic activity. MCF-7 cells are transfected with the indicated plasmids and then assayed for apoptosis as in FIG. 3A.
Figure 5B:
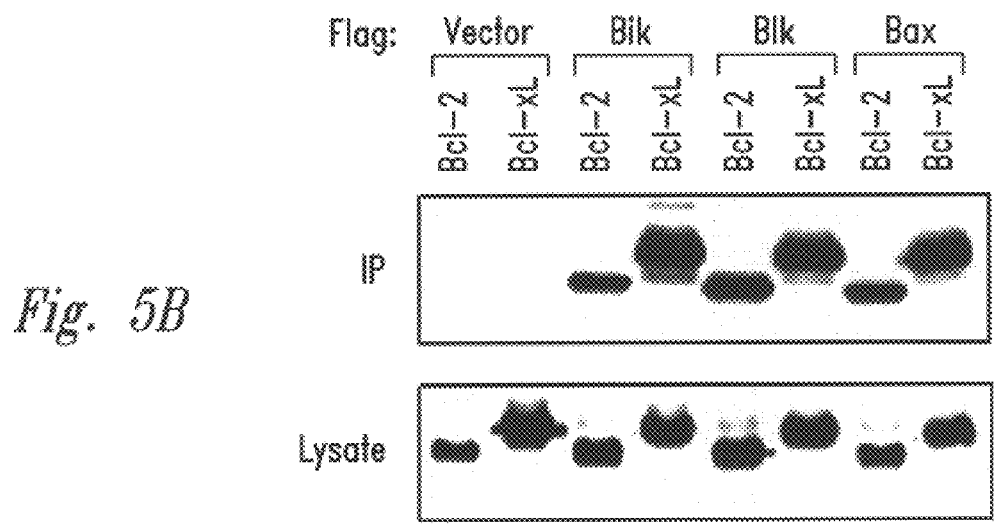

$^{35}$S-labeled Blk, Bik or Bax are precipitated with glutathione S-transferase (GST), GST-Bcl-2 or GST-Bcl-xL fusion proteins immobilized on glutathione-Sepharose beads (FIG. 5A). Like Bik and Bax, Brk specifically associates with GST-Bcl-2 and GST-Bcl-xL, but not with the GST control. This evidences that Blk interacts directly with Bcl-2 and Bcl-xL. Similarly, Blk, Bik and Bax bind to Bcl-2 and Bcl-xL when these proteins are co-expressed in vivo (FIG. 5B).

Mutations in the BH3 domain affect function. The BH3 domain of Blk is critical for its proapoptotic activity and interaction with Bcl-2 and Bcl-xL. In view of the importance of the BH3 domain in the death agonist activity of the proapoptotic Bcl-2 family members, mutations are introduced in the BH3 domain of Blk to identify critical residues for its function.

The conserved amino acids in the BH3 domain, Leu55 and Gly59-Asp60 of Blk are mutated by site directed mutagenesis using overlapping amplification as described before (Srinivasula et al., *J. Biol Chem.* 271: 27099, 1996). Two Blk mutants are constructed, in which either Gly59 (Blk-DG59) or Gly59 and Asp60 (Blk-DG59-D60) are deleted. The amplified products are cloned in the pFLAG CMV-2 and pRSC-double vector and mutations are confirmed by DNA sequence analysis.

Figure 5C:
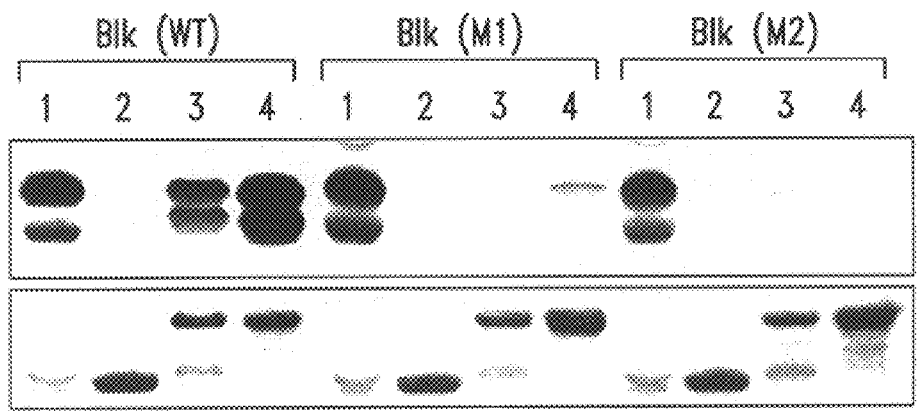
Figure 5D:
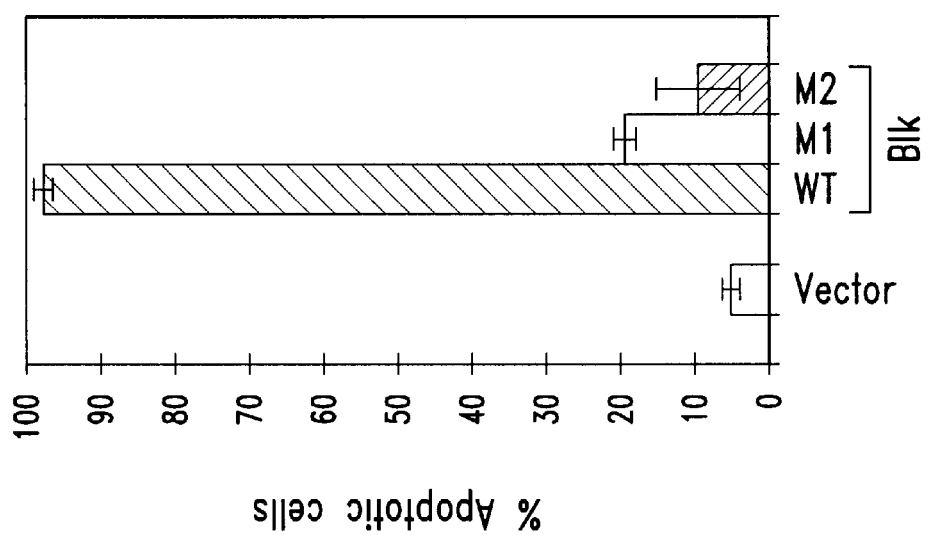

As shown in FIGS. 5C and D, Blk-DG59 shows drastic reduction in both binding to Bcl-2 and Bcl-xL and death agonist activity. Deletion of Gly59-Asp60 also abrogates both activities, consistent with observations using Bak (Chittenden et al., *EMBO J.* 14: 5589, 1995). This demonstrates the importance of these residues in keeping the overall geometry of the BH3 domain, and further confirms the critical role of the BH3 domain in the death agonist activity of Blk.

Figure 6A:
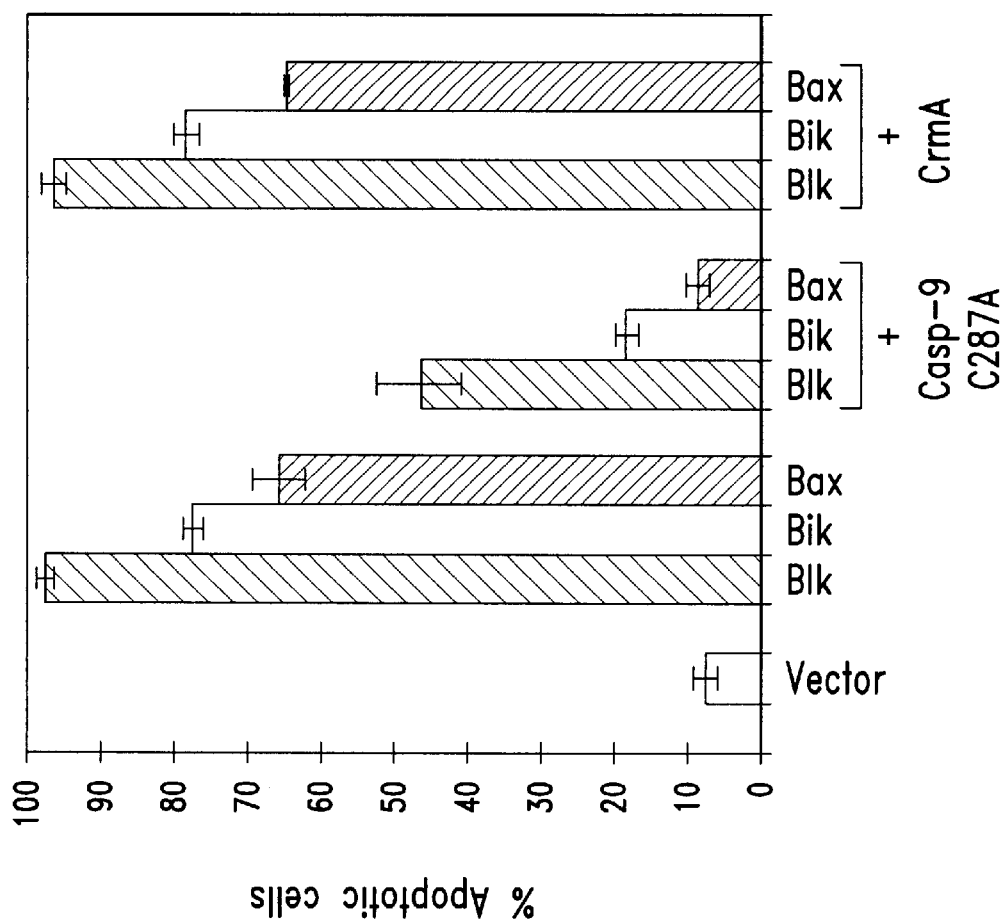
FIGS. 6A and B show inhibition of Blk-, Bik- and Bax-induced apoptosis and caspase-3 activation by an active site mutant of caspase-9. MCF-7 and 293 cells are transiently transfected with the indicated plasmids in combination with a four-fold excess of caspase-9 C287A or CrmA. (A) The graph shows the percentage of round blue apoptotic MCF-7 cells (mean±SD) as a function of total blue cells under each condition ($n^3$ 3). (B) Human 293 cells are transfected with the indicated expression plasmids and 30 hr after transfection cell lysates are prepared and analyzed by Western blot analysis using a polyclonal antibody against human caspase-3 p20 (upper panel) or a monoclonal antibody to the Flag-epitope (lower panel).

Mutations in Caspase-9 affect Blk function. Cytochrome c release from the mitochondria and its binding to Apaf-1 triggers a dATP/ATP-dependent activation of caspase-9, the most upstream caspase in the cytochrome c-dependent apoptotic pathway, which can be blocked by an active site dominant negative caspase-9 mutant (Li et al., *Cell* 91: 627, 1997) or by Bcl-2 and Bcl-xL (Reed, *Cell* 91: 479, 1997). To determine whether the cytochrome c/Apaf-1/caspase-9 pathway is involved in Blk-induced apoptosis, MCF-7 cells are co-transfected with Blk, Bik or Bax and an inactive caspase-9 C287A mutant. Overexpression of Blk, Bik or Bax induced apoptosis in nearly 97%, 78% or 70% of the cells, respectively (FIG. 6A). The active site mutant of caspase-9 reduces the percentage of cells undergoing apoptosis to nearly 52%, 20% or 10% respectively. When the caspase-9 mutant is substituted with caspase-8 or caspase-10 dominant negative mutants that block death receptor-induced apoptosis, no protection is observed. Furthermore, CrmAICE inhibitor (it is a serpin), which inhibits caspase-8, but not caspase-9, is also ineffective against Blk-, Bik- and Bax-induced apoptosis (FIG. 6A). Thus, an active site mutation of caspase-9 blocks Blk, Bik and Bax-induced apoptosis.

Figure 6B:
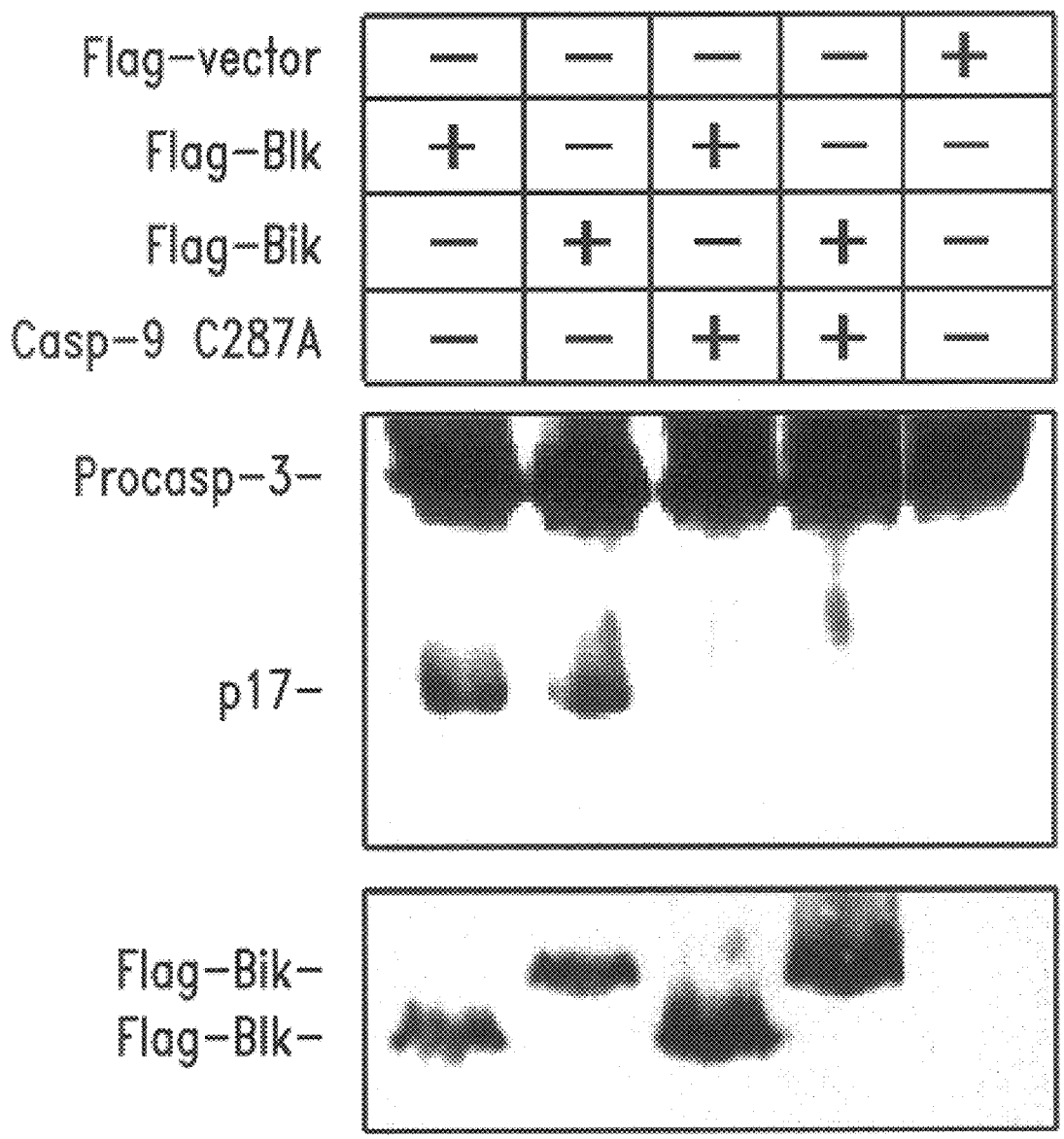

Binding of the active site mutant of caspase-9 to the Apaf-1/cytochrome c complex inactivates this complex and blocks apoptosis by inhibiting activation of the downstream caspase-3, which is directly activated by caspase-9. Consistent with this, the caspase-9 mutant can inhibit Bax-induced apoptosis and processing of caspase-3. Furthermore, like Bax, transfection of 293 cells with Blk or Bik results in processing of caspase-3 (FIG. 6B). This processing is almost completely blocked when a 4-fold excess of mutant caspase-9 is co-expressed with Blk or Bik (FIG. 6B). Processing of caspase-7 is also inhibited in these cells by the caspase-9 mutant, suggesting that caspase-3 and 7 are downstream of caspase-9 in Blk-induced apoptosis. Taken together, caspase-9 appears to be the most upstream caspase in the apoptotic pathway triggered by the proapoptotic Bcl-2 family members.

In conclusion, Blk is identified as a novel member of the Bcl-2 family of death regulatory proteins. Like Bik, Bid and Hrk, Blk shares sequence homology with other family members in the BH3 domain, but lacks the conserved BH1, BH2 and BH4 domains. The BH3 domain is essential for the death agonist activity of Blk and its ability to interact with Bcl-2 and Bcl-xL, since deletions of conserved residues in this domain abolish both activities. This provides evidence that direct interactions between the BH3 domain of Blk and Bcl-2 or Bcl-xL is required to suppress the protective activity of these proteins and induce apoptosis. Blk, Bik and Bax may induce apoptosis by triggering the formation of the Apaf-1/caspase-9 complex and activation of caspase-9, downstream of Bcl-2 and Bcl-xL, possibly by triggering cytochrome c release from the mitochondria by inhibiting the channel forming activity of Bcl-2 or Bcl-xL, leading to disruption of the outer mitochondrial membrane.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising SEQ ID NO:2, or a variant thereof, said variant having at least 90% sequence identity with SEQ ID NO:2 and comprising SEQ ID NO:3, and wherein said variant induces apoptosis, binds Bcl-2 and Bcl-xL.

2. An isolated BH3 domain of a Blk polypeptide, wherein the BH3 domain consists of sequence Ala Leu Arg Leu Ala Cys Ile Gly Asp Glu Met Asp (SEQ ID NO:3).

3. A composition comprising a polypeptide of SEQ ID NO:2, or a variant thereof, said variant having at least 90% sequence identity with SEQ ID NO:2 and comprising SEQ ID NO:3, wherein said variant induces apoptosis, binds Bcl-2 and Bcl-xL and a physiologically acceptable carrier.

4. A composition comprising an isolated BH3 domain of a Blk polypeptide, wherein the BH3 domain consists of sequence Ala Leu Arg Leu Ala Cys Ile Gly Asp Glu Met Asp (SEQ ID NO:3), wherein said SEQ ID NO:3 contains one or more amino acid substitutions, wherein the second Leu, the Gly, and the first Asp residues are not substituted; and a physiologically acceptable carrier.

* * * * *

UNITED STATES PATENT AND TRADEMARK OFFICE
CERTIFICATE OF CORRECTION

| | |
|---|---|
| PATENT NO. | : 6,600,024 B1 |
| APPLICATION NO. | : 09/709790 |
| DATED | : July 29, 2003 |
| INVENTOR(S) | : Emad S. Alnemri |

It is certified that error appears in the above-identified patent and that said Letters Patent is hereby corrected as shown below:

In the Specification

On Column 1, Lines 10-14, please replace the existing section with the following:
-- ACKNOWLEDGEMENT OF GOVERNMENT RIGHTS This invention was made with government support under AG014357, and AG013487 awarded by the National Institutes of Health. The government has certain rights in the invention. --

Signed and Sealed this
Twenty-fifth Day of February, 2025

Coke Morgan Stewart
*Acting Director of the United States Patent and Trademark Office*